US011536817B2

(12) United States Patent
Solek et al.

(10) Patent No.: US 11,536,817 B2
(45) Date of Patent: Dec. 27, 2022

(54) ULTRASONIC IMAGING PROBE INCLUDING COMPOSITE APERTURE RECEIVING ARRAY

(71) Applicant: INTERSON CORPORATION, Pleasanton, CA (US)

(72) Inventors: Roman Solek, Pleasanton, CA (US); Patrice Richard, Pleasanton, CA (US); Albert Lee, Pleasanton, CA (US)

(73) Assignee: INTERSON CORPORATION, Pleasanton, CA (US)

( * ) Notice: Subject to any disclaimer, the term of this patent is extended or adjusted under 35 U.S.C. 154(b) by 0 days.

(21) Appl. No.: 17/080,405

(22) Filed: Oct. 26, 2020

(65) Prior Publication Data
US 2021/0041545 A1 Feb. 11, 2021

Related U.S. Application Data

(63) Continuation of application No. 15/484,478, filed on Apr. 11, 2017, now Pat. No. 10,816,650.
(Continued)

(51) Int. Cl.
G01S 7/52 (2006.01)
G10K 11/34 (2006.01)
(Continued)

(52) U.S. Cl.
CPC ............ *G01S 7/52022* (2013.01); *A61B 8/14* (2013.01); *A61B 8/4444* (2013.01);
(Continued)

(58) Field of Classification Search
CPC . G01S 7/52; G01S 15/89; G01S 7/524; G01S 7/52085; G01S 7/52022;
(Continued)

(56) References Cited

U.S. PATENT DOCUMENTS 4,140,022 A 2/1979 Maslak
4,159,462 A 6/1979 Rocha
(Continued)

FOREIGN PATENT DOCUMENTS

WO 2005038449 4/2005

OTHER PUBLICATIONS

European Patent Office, International Searching Authority, International Search Report and Written Opinion dated Nov. 5, 20107 for International Application No. PCT/US2007/061996, 9 Pages.
(Continued)

*Primary Examiner* — Isam A Alsomiri
*Assistant Examiner* — Amie M Ndure
(74) *Attorney, Agent, or Firm* — Tucker Ellis LLP

(57) ABSTRACT

A system and method from improving the image quality achievable with an ultrasound transducer by using a composite aperture for receiving ultrasound echoes. By using two receive cycles per vector, twice as many transducers may be used for receiving ultrasound imaging data than there are physical channels available in the ultrasound probe. An ultrasound probe utilizing a composite aperture can achieve high image quality from a system have reduced power, size, cost and complexity.

17 Claims, 8 Drawing Sheets

Related U.S. Application Data

(60) Provisional application No. 62/342,347, filed on May 27, 2016.

(51) Int. Cl.
    *G01S 15/89*     (2006.01)
    *A61B 8/14*     (2006.01)
    *A61B 8/00*     (2006.01)
    *B06B 1/02*     (2006.01)
    *B06B 1/06*     (2006.01)
    *G01S 7/524*     (2006.01)

(52) U.S. Cl.
CPC .......... *A61B 8/4483* (2013.01); *A61B 8/461* (2013.01); *B06B 1/0215* (2013.01); *B06B 1/0622* (2013.01); *G01S 7/524* (2013.01); *G01S 7/52085* (2013.01); *G01S 15/8918* (2013.01); *G01S 15/8927* (2013.01); *G10K 11/341* (2013.01); *G10K 11/346* (2013.01); *B06B 2201/56* (2013.01); *B06B 2201/76* (2013.01); *G01S 7/52082* (2013.01); *G01S 7/52096* (2013.01)

(58) Field of Classification Search
CPC .......... G01S 15/8927; G01S 15/8918; G01S 7/52082; G01S 7/52096; A61B 8/00; A61B 8/14; A61B 8/461; A61B 8/4483; A61B 8/4444; B06B 1/02; B06B 1/06; B06B 1/0622; B06B 1/0215; B06B 2201/76; B06B 2201/56; G10K 11/34; G10K 11/341; G10K 11/346

See application file for complete search history.

(56) References Cited

U.S. PATENT DOCUMENTS

| | | |
|---|---|---|
| 4,530,363 A | 7/1985 | Brisken |
| 4,589,284 A | 5/1986 | Breimesser |
| 4,773,426 A | 9/1988 | Molnar |
| 4,953,147 A | 8/1990 | Cobb |
| 5,369,890 A | 12/1994 | Malz |
| 5,394,750 A | 3/1995 | Matzuk |
| 5,563,346 A | 10/1996 | Bartelt |
| 5,613,493 A | 3/1997 | Schafer |
| 5,647,367 A | 7/1997 | Lum |
| 5,795,297 A | 8/1998 | Daigle |
| 5,840,032 A | 11/1998 | Hatfield |
| 5,913,447 A | 6/1999 | Carpenter |
| 6,012,332 A | 1/2000 | Schafer |
| 6,013,032 A | 1/2000 | Savord |
| 6,045,508 A | 4/2000 | Hossack |
| 6,099,474 A | 8/2000 | Solek |
| 6,113,545 A | 9/2000 | Chiao |
| 6,120,454 A | 9/2000 | Suorsa |
| 6,213,948 B1 | 4/2001 | Barthe |
| 6,238,346 B1 | 5/2001 | Mason |
| 6,381,197 B1 | 4/2002 | Savord |
| 6,398,734 B1 | 6/2002 | Cimochowski |
| 6,440,071 B1 | 8/2002 | Slayton |
| 6,458,073 B1 | 10/2002 | Bonthuys |
| 6,524,244 B1 | 2/2003 | Knell |
| 6,595,921 B1 | 7/2003 | Urbano |
| 6,719,693 B2 | 4/2004 | Richard |
| 6,865,140 B2 | 3/2005 | Thomenius |
| 6,887,204 B2 | 5/2005 | Nozaki |
| 6,969,352 B2 | 11/2005 | Chiang |
| 6,974,417 B2 | 12/2005 | Lockwood |
| 7,484,412 B2 | 2/2009 | Hart |
| 7,489,593 B2 | 2/2009 | Nguyen-Dinh |
| 7,673,479 B2 | 3/2010 | Dahlheimer |
| 8,114,024 B2 | 2/2012 | Solek |
| 8,500,641 B2 | 8/2013 | Raju |
| 2003/0028109 A1 | 2/2003 | Miller |
| 2003/0045794 A1* | 3/2003 | Bae ............... G01S 7/52047 600/437 |
| 2004/0015079 A1 | 1/2004 | Berger |
| 2004/0195778 A1 | 10/2004 | Smith |
| 2005/0228281 A1 | 10/2005 | Nefos |
| 2006/0145426 A1 | 7/2006 | Schroeder |
| 2007/0239019 A1 | 10/2007 | Richard |
| 2008/0255451 A1 | 10/2008 | Cohen |
| 2008/0300490 A1 | 12/2008 | Chiang |
| 2011/0295119 A1 | 12/2011 | Miller |
| 2013/0296693 A1* | 11/2013 | Wenzel ............ A61B 34/20 600/521 |
| 2013/0296743 A1* | 11/2013 | Lee ............... G16H 50/30 601/3 |
| 2013/0304405 A1* | 11/2013 | Schmid .......... A61B 5/721 702/56 |
| 2013/0308137 A1* | 11/2013 | Manzke .......... A61B 34/20 356/511 |
| 2013/0308850 A1* | 11/2013 | Oikawa ........ G01S 15/8945 382/131 |
| 2014/0031693 A1* | 1/2014 | Solek ............. A61B 8/145 600/447 |
| 2014/0031694 A1 | 1/2014 | Solek |
| 2015/0216511 A1* | 8/2015 | Tur ............... A61B 8/565 600/443 |
| 2015/0241397 A1 | 8/2015 | Savord |

OTHER PUBLICATIONS

Angelsen, Bjorn A.J., et al., "Which transducer array is best?", European Journal of Ultrasound 2 (1995) 151-164.

AD8310 Datasheet, "Fast, Voltage-Out DC-440 MHz, 95 dB Logarithmic Amplifier," Analog Devices, Inc. (2005), http://www.analos.com/UploadedFileslData Sheets181 5636058AD8310 e.pdf.

EZ-USB FX2LP USB Microcontroller Datasheet, Cypress Semiconductor Corporation (2005), http://fp.cse.wustl.edu/cse462/Downloads/c7c68013a 5.pdf.

Johnson, Jeremy et al., "Medical imaging using capacitive micromachined ultrasonic transducer arrays", Ultrasonics 40 (2002) 471-476.

Johnson, Jeremy et al., "Coherent-Array Imaging Using Phased Subarrays. Part I: Basic Principles", IEEE Transactions on Ultrasonics, Ferroelectrics, and Frequency Control, vol. 52, No. 1, Jan. 2005 (37-50).

Khuri-Yakub, Butrus et al., "Next-Gen Ultrasound", spectrum.ieee.org. Retrieved Jul. 12, 2012, from http://spectrumieee.org/biomedical/imaging/nextgen-ultrasound/0.

Khuri-Yakub, B. (Pierre) T., "MEMS based ultrasonic transducers in medical imaging, therapy and sensing", parc.com. Retrieved Jul. 12, 2012 from http://www.parc.com/event/642/mems-based-ultrasonic-transducers-in-medical-imaging-therapy-and-sensing.html.

Richard, W.D., "A New Time-Gain Correction Method for Standard B-Mode Ultrasound Imaging," IEEE Transactions on Medical Imaging, vol. 8, pp. 283-285, Sep. 1989.

Richard, W.D. and R.M. Arthur, "Real-Time Ultrasonic Scan Conversion via Linear Interpolation of Oversampled Vectors," Ultrasonic Imaging, vol. 16, pp. 109-1 23, Apr. 1994.

Richard, W.D., et al., "A Low-cost B-Mode USB Ultrasound Probe", Ultrasonic Imaging, vol. 30, 9 p. 2008.

Seagar, Andrew Dr., "Basic Principles of Ultrasound Imaging System Design", Biomedical Imaging HET408, Mar. 25, 2002, 22 pages.

Nguyen-Dinh, An, "From MEMS devices to Medical Diagnostic Market. A case study: Ultrasonic Imaging", Mar. 2011, Presentation by An Nguyen-Dinh, Director of Technology, Vermon SA, France, 20 pages.

Wong, Serena H. et al., "Evaluation of Wafer Bonded CMUTs with Rectangular Membranes Featuring High Fill Factor", IEEE Transactions on Ultrasonics, Ferroelectrics and Frequency Control, vol. 55, No. 9, Sep. 2008, 2053-2065.

Wygant, Ira O, et al., "Integration of 2D CMUT Arraays with Front-End Electronics for Volumetric Ultrasound Imaging", IEEE

(56) References Cited

OTHER PUBLICATIONS

Transactions on Ultrasonics, Ferroelectrics, and Frequency Control., vol. 55, No. 2, Feb. 2008, 327-342.

* cited by examiner

Figure 2B
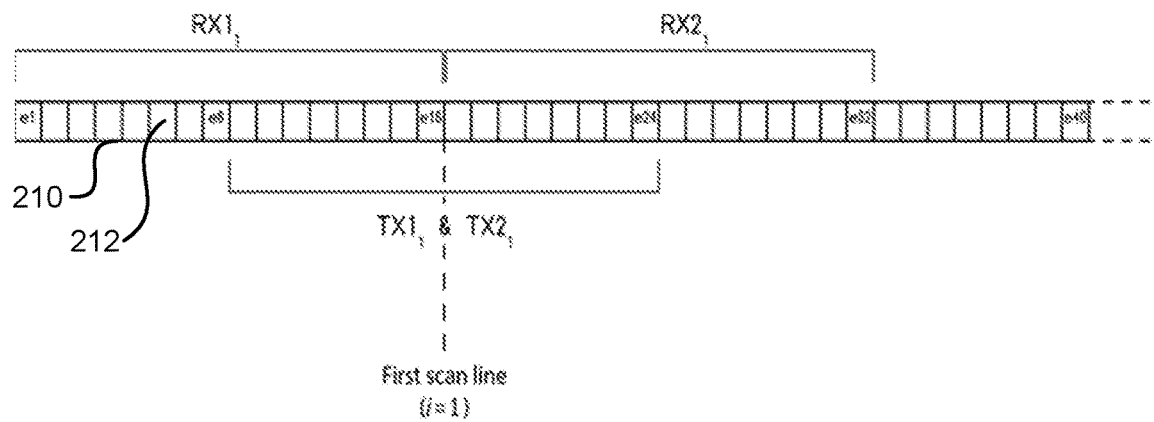
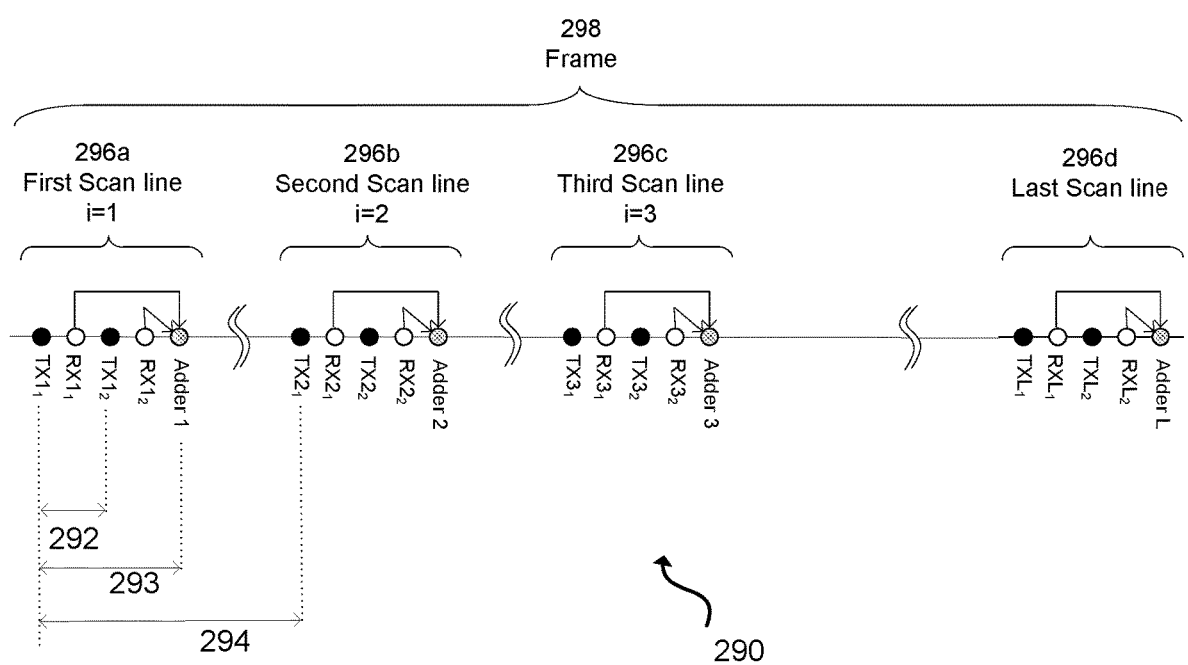
Figure 2C

Pulse 1

Echo 1

Pulse 2

Echo 2

Figure 4

| Line | Time | Transmit (TX) | Receive (RX) | Add Half Lines | Group of Elements | Position of scan line | Type of Focus | Write to Half Line Buffer 1 | Write to Half Line Buffer 2 | Write to Full Line Buffer |
|---|---|---|---|---|---|---|---|---|---|---|
| 1 | TX1₁ | x | | | 9 to 24 | 16.5 | Fixed | | | |
| | RX1₁ | | x | | 1 to 16 | 16.5 | Dynamic | x | | |
| | TX2₁ | x | | | 9 to 24 | 16.5 | Fixed | | | |
| | RX2₁ | | x | | 17 to 32 | 16.5 | Dynamic | | x | |
| | FLA₁ | | | x | - | | | | | x |
| 2 | TX1₂ | x | | | 10 to 25 | 17.5 | Fixed | | | |
| | RX1₂ | | x | | 2 to 17 | 17.5 | Dynamic | x | | |
| | TX2₂ | x | | | 10 to 25 | 17.5 | Fixed | | | |
| | RX2₂ | | x | | 18 to 33 | 17.5 | Dynamic | | x | |
| | FLA₂ | | | x | - | | | | | x |
| 3 | TX1₃ | x | | | 11 to 26 | 18.5 | Fixed | | | |
| | RX1₃ | | x | | 3 to 18 | 18.5 | Dynamic | x | | |
| | TX2₃ | x | | | 11 to 26 | 18.5 | Fixed | | | |
| | RX2₃ | | x | | 19 to 34 | 18.5 | Dynamic | | x | |
| | FLA₃ | | | x | - | | | | | x |
| ... | | | | | | | | | | |
| 33 | TX1₃₃ | x | | | 41 to 56 | 48.5 | Fixed | x | | |
| | RX1₃₃ | | x | | 33 to 48 | 48.5 | Dynamic | | | |
| | TX2₃₃ | x | | | 41 to 56 | 48.5 | Fixed | | | |
| | RX2₃₃ | | x | | 49 to 64 | 48.5 | Dynamic | | x | |
| | FLA₃₃ | | | x | - | | | | | x |

ULTRASONIC IMAGING PROBE INCLUDING COMPOSITE APERTURE RECEIVING ARRAY

CLAIM OF PRIORITY

The present application is a continuation of U.S. patent application Ser. No. 15/484,478, filed Apr. 11, 2017 entitled "ULTRASONIC IMAGING PROBE INCLUDING COMPOSITE APERTURE RECEIVING ARRAY" and which claims the benefit of priority to U.S. Provisional Patent Application No. 62/342,347, filed May 27, 2016 entitled "ULTRASONIC IMAGING PROBE INCLUDING COMPOSITE APERTURE RECEIVING ARRAY", which applications are incorporated herein by reference in their entirety.

FIELD OF THE INVENTION

The present invention relates to portable ultrasonic imaging probes, and more specifically, to such probes including a transducer array, wherein such probes can be directly connected to a host computer, such as an off-the-shelf laptop computer, or the like.

BACKGROUND

Typically, ultrasound imaging systems include a handheld probe that is connected by a cable to a relatively large and expensive piece of hardware that is dedicated to performing ultrasound signal processing and displaying ultrasound images. Such systems, because of their high cost, are typically only available in hospitals or in the offices of specialists, such as radiologists. Recently, there has been an interest in developing more portable ultrasound imaging systems that can be used with personal computers. Preferably, such a portable ultrasound probe can be used with an off-the-shelf host computer, such as a personal computer, and is inexpensive enough to provide ultrasound imaging capabilities to general practitioners and health clinics having limited financial resources.

For producing high quality ultrasound images it is generally considered desirable to provide an ultrasound probe having 32 channels or more. However, each channel typically requires dedicated electronics and 100 mW of power to operate. Thus the power requirements for a 32 channel probe typically exceed the power available for devices powered by USB 2.0, which provides up to 2.5 W, or integrated rechargeable batteries. Such devices are therefore usually limited to sixteen channels consequently limiting the quality of images they can produce. Moreover, the electronics required to operate 32 channels in an ultrasound add to the size, complexity and cost of the ultrasound probe.

It is therefore desirable to achieve the image quality of a 32 channel ultrasound probe while limiting power consumption.

It is also desirable to enable production of low power portable ultrasound probes with reduced sized, complexity and cost while still achieving high quality imaging.

SUMMARY OF THE INVENTION

The present application describes systems and methods for implementing low power portable ultrasound probes with reduced sized, complexity and cost while still achieving high quality imaging. The disclosed systems and methods enable ultrasound probes to achieve the image quality of a 32 channel ultrasound probe while limiting power consumption.

In accordance with embodiments, the present application describes an ultrasonic imaging probe which utilizes a composite aperture receiving array which doubles the effective number of receive channels. The probe implements a method for patterning the transmit and receive cycles of an ultrasonic array which allows the receiving aperture to utilize twice the number of array elements as there are receive channels, improving focus, quality, and depth of the image without increasing the power consumption. The result is a single received signal that is equivalent to a signal received by a system with twice the number of channels. Essentially, the composite aperture comprises two receive apertures used one after the other to receive ultrasound echoes from two identical ultrasound pulses emitted in quick succession and then combined to generate an echo signal equivalent to a receive aperture of double the size of the two receive apertures individually.

In accordance with embodiments, the composite aperture receiving array can be implemented in portable low power ultrasound probe. For ultrasound probes, 32 receive channels is generally considered the minimum for producing high quality images, with each channel typically requiring 100 mW of power. Devices powered by USB 2.0, which provides up to 2.5 W, or integrated rechargeable batteries only have enough power for sixteen channels. Using the composite aperture technology as described in this invention, lower power devices can be designed to produce ultrasound images having the equivalent image quality as a 32 channel system while utilizing only sixteen physical channels simultaneously. The increased aperture size, as a result of the composite aperture, improves enhanced image resolution. The use of only sixteen physical channels also reduces power consumption, complexity and cost of the low power ultrasound probe. Composite apertures as disclosed herein allow for the use of smaller and lighter electronics that can be fully integrated into ergonomic hand held devices that connect to host devices via passive interfaces. Product costs are reduced by the use of composite apertures because fewer receiving channels and their associated components need to be used.

Other objects and advantages of the present invention will become apparent to those skilled in the art from the following description of the various embodiments, when read in light of the accompanying drawings.

BRIEF DESCRIPTION OF THE DRAWINGS

Various embodiments of the present invention can be described in detail based on the following figures, wherein:

FIG. 2B illustrates operation of the system shown in the block diagram of FIG. 2A.

FIG. 2C shows a timeline for operation of the system shown in the block diagram of FIG. 2A.

FIG. 4 shows a timing diagram for an example system according to an embodiment of the present invention.

DETAILED DESCRIPTION

Figure 1A:
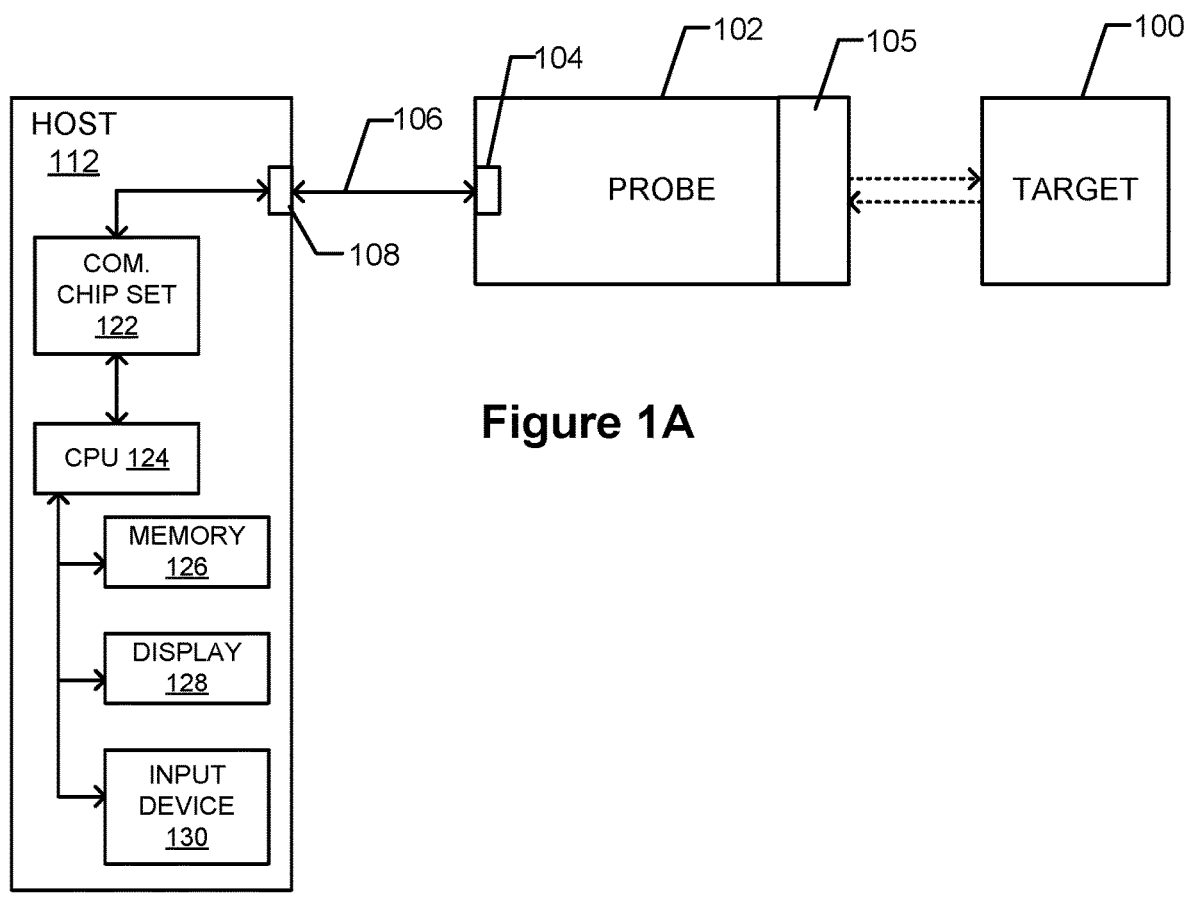
FIG. 1A shows a high level diagram showing an ultrasonic imaging system.

In the following description, the invention will be illustrated by way of example and not by way of limitation in the figures of the accompanying drawings. References to various embodiments in this disclosure are not necessarily to the same embodiment, and such references mean at least one. While specific implementations are discussed, it is understood that this is provided for illustrative purposes only. A person skilled in the relevant art will recognize that other components and configurations may be used without departing from the scope and spirit of the invention. Furthermore, in certain instances, numerous specific details will be set forth to provide a thorough description of the invention. However, it will be apparent to those skilled in the art that the invention may be practiced without these specific details. In other instances, well-known features have not been described in as much detail so as not to obscure the invention.

Common reference numerals are used to indicate like elements throughout the drawings and detailed description; therefore, reference numerals used in a figure may or may not be referenced in the detailed description specific to such figure if the element is described elsewhere. The first digit in a three digit reference numeral indicates the series of figures in which the element first appears.

FIG. 1A shows an ultrasonic imaging probe 102, according to an embodiment of the present invention, which is connected by an interface cable 106 to a host computer 112. Ultrasonic imaging probe 102 includes an array of ultrasound transducers for transmitting and receiving ultrasound pulses as will be described below. The ultrasonic array in combination with the electronics of ultrasonic imaging probe implements a composite aperture receiving array in order to produce high quality imaging data.

The host computer 112 can be a desktop personal computer (PC), a laptop PC, a pocket PC, a tablet PC, a mobile phone capable or running software programs (often referred to as a "smart phone"), a personal digital assistant, or the like. The interface cable 106, which includes connectors and wires, can be a Universal Serial Bus (USB) cable (e.g., a USB 2.0 cable), a FireWire (also known as IEEE 1394) cable, or the like. Preferably the probe 102 is not connected to any other device or power supply. Thus, in a preferred embodiment the probe 102 receives all its necessary power from the host computer 112 via the passive interface cable 106. In alternative embodiments, probe 102 can include a battery and a wireless transceiver, in which case the probe can wirelessly communicate with the host computer, and the probe will draw all its necessary power from the battery.

As will be described in more detail below, in accordance with embodiments of the present invention, the probe 102 enables the host computer 112, via software running on the host computer 112, to form real-time ultrasonic images of a target 100 (e.g., human tissue or other materials) without the need for any additional internal or external electronics, power supply, or support devices. In certain embodiments, the probe 102 produces raw digitized data that is envelope detected ultrasound echo data from an array of ultrasound transducers in the probe 102, and transmits such raw data to the host computer 112. The raw digitized data can optionally also be logarithmically compressed, depending upon implementation.

In an embodiment, when the host computer 112 receives raw data via the passive interface cable 106 from the probe 102, the host computer 112 performs time gain compensation, gray-scale mapping, and scan conversion of the raw data using software that runs on the host computer 112, and displays the resultant video images. The probe does not include any moving mechanical parts, thereby reducing the complexity and cost of the probe 102 and increasing its reliability. The term "raw data", as used herein, refers to digital ultrasound imaging data that has not yet been time gain compensated, gray-scale mapped and scan converted. As described below, such raw data is included in the digital signal that is transferred from the probe 102 to the host computer 112.

As shown in FIG. 1A, the host computer 112 will likely include a communications port 108, a communications chip-set 122, a central processing unit (CPU) 124, memory 126, a display 128, and an input device 130, such as a keyboard, mouse, touch screen, track ball, or the like. Additionally, the host computer 112 runs software that enables the host to control specific aspects of the probe 102. Such software also enables the host computer 112 to perform time gain compensation (also known as time gain correction), gray-scale mapping, and scan conversion of the raw data received from the probe 112 over the passive interface cable 106. The host computer 112 can then display the resulting ultrasound video on the display 128, as well as store such video in its memory 126, or another data storage device (not shown).

The article "A New Time-Gain Correction Method for Standard B-Mode Ultrasound Imaging", by William D. Richard, *IEEE Transactions of Medical Imaging*, Vol. 8, No. 3, pp. 283-285, September 1989, which is incorporated herein by reference, describes an exemplary time gain correction technique that can be performed by the host computer 112. The article "Real-Time Ultrasonic Scan Conversation via Linear Interpolation of Oversampled Vectors," *Ultrasonic Imaging*, Vol. 16, pp. 109-123, April 1994, which is incorporated herein by reference, describes an exemplary scan conversion technique that can be performed by the host computer 112. These are just exemplary details of the host computer 112, which are not meant to be limiting.

The interface cable 106 includes one or more data line over which data is carried, and at least one power line to provide power to a peripheral device, which in this case is the ultrasonic imaging probe 102. For example, where the interface cable 106 is a USB 2.0 cable, one wire of the cable provides about 5V at about ½ Amp. In alternative embodiments, the interface cable 106 is a Firewire cable, which also includes a power wire. Other types of interface cable having 16, 32 or more signal wires can be used if desired. However, it is preferred that the passive interface cable 106 is a standard off-the-shelf cable that can interface with an off-the-shelf interface IC. The term passive as used herein refers to a cable that does not regenerate signals or process them in any way. In an alternative embodiment, the probe 102 and the host computer 112 communicate wirelessly, and the probe 102 includes a battery that is used to power the components within the probe.

Whether the probe is battery powered, or powered over a cable from a computer, the amount of power available to operate the probe is constrained. Accordingly, portable ultrasound probes typically have used only a small number of ultrasound transducers to send and receive ultrasound at any point in time. This conserves power but also reduces the image quality as compared to non-power constrained probes which can operate many transducers simultaneously for sending and receiving ultrasound signals. As described below, the present disclosure describes systems and methods which increase the number of transducers which can be effectively used, increasing the image quality while operating within the constraints of power available.

Figure 1B:
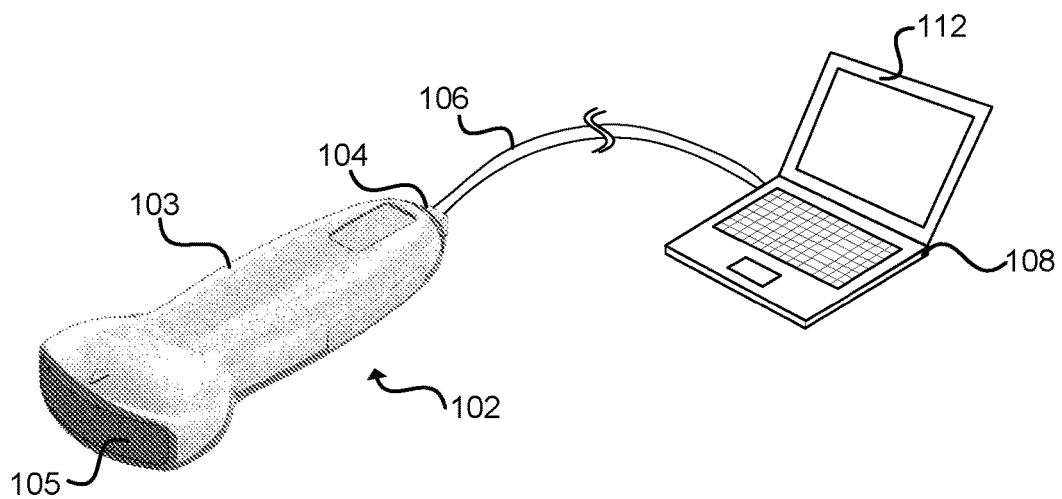
FIG. 1B illustrates an ultrasonic imaging probe according to an embodiment of the present invention.

FIG. 1B illustrates an example where the host computer 112 is a laptop. FIG. 1B also shows an exemplary ergonomic design of a housing 103 for the ultrasonic imaging probe 102 of the present invention. Other ergonomic designs are of course possible, and within the scope of the present invention. Also, as explained above, other types of host computer 112 can also be used. FIG. 1B also shows that the ultrasonic imaging probe 102 includes a probe head assembly 105. Probe head assembly 105 comprises an array of piezoelectric ultrasound transducers for transmitting and receiving ultrasound pulses as will be described below. The ultrasonic array in combination with the electronics of ultrasonic imaging probe implements a composite aperture receiving array in order to produce high quality imaging data.

In accordance with certain embodiments, the data samples produced by the ultrasonic imaging probe 102 of the present invention are transmitted by the probe 102 across the interface cable 106 to the host computer 112. The host computer 112 runs software that enables the host to perform time gain compensation, gray-scale mapping, and scan conversion of the data received from the probe 102. The host computer generates and displays the resultant ultrasound video images. Advantageously, the host computer 112 does not need to perform electronic beamforming or other equivalent image processing, thereby simplifying the software that the host computer 112 runs.

The host computer 112 can use the digital data received from the ultrasound device 102 to provide any available type of ultrasound imaging mode can be used by the host computer 112 to display the ultrasound images, including, but not limited to A-mode, B-mode, M-mode, etc. For example, in B-mode, the host computer 112 performs know scan conversion such that the brightness of a pixel is based on the intensity of the echo return.

A benefit of specific embodiments of the present invention is that only digital signals are transmitted from the probe 102 to the host computer 112, thereby providing for better signal-to-noise ratio than if analog signals were transmitted from the probe 102 to the host computer 112, or to some intermediate apparatus between the host computer and the probe.

Figure 2A:
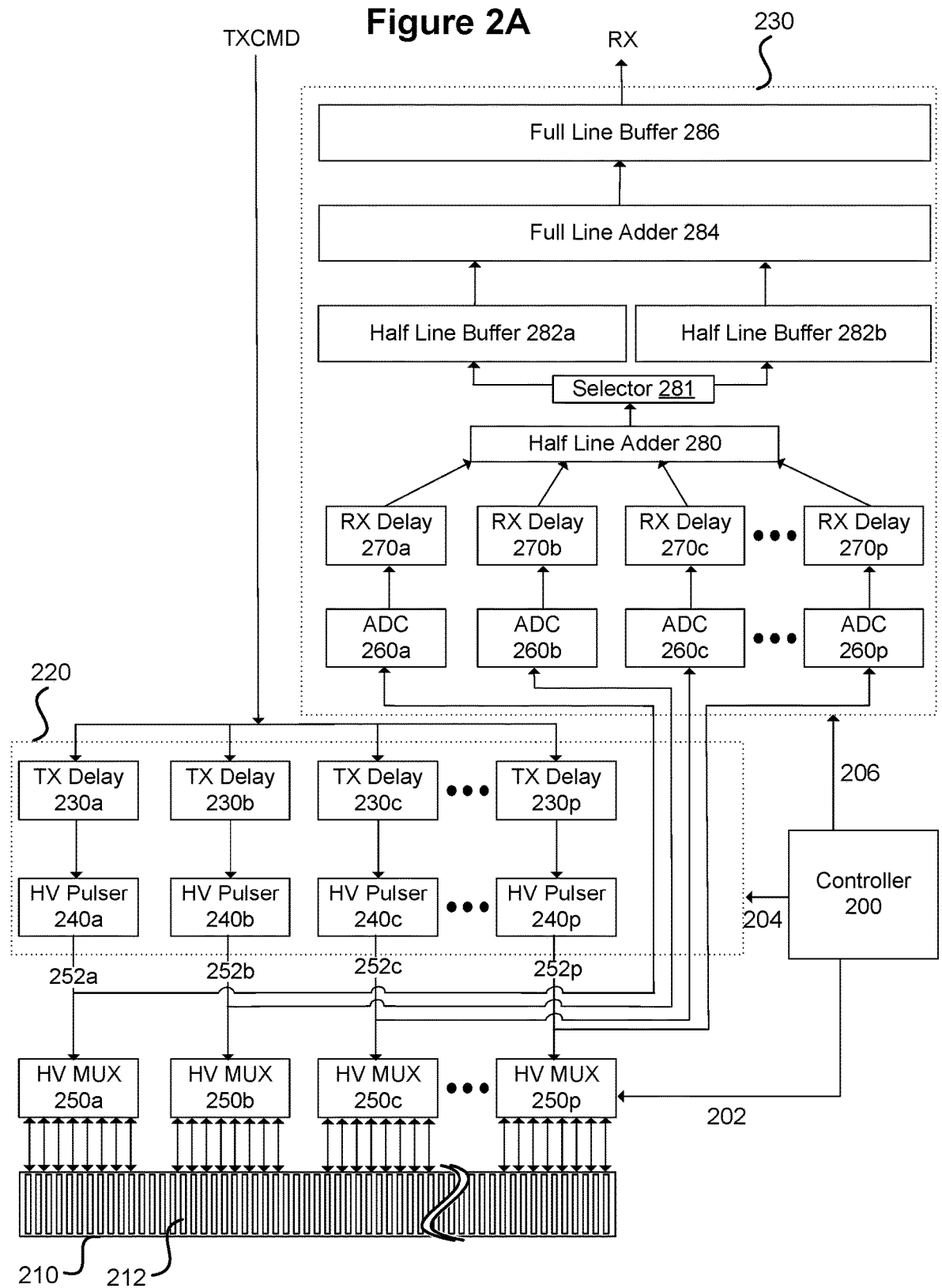
FIG. 2A is a block diagram that shows additional details of an ultrasonic imaging probe according to an embodiment of the present invention.

FIG. 2A is a block diagram that shows additional details of an ultrasonic imaging probe according to an embodiment of the present invention. FIG. 2 shows an example of a system which implements a composite aperture receiver which provides for 32 receiving channels from a system that utilizes only sixteen channels at any point in time of a 128 element transducer array. Transducer array 210 includes 128 transducer elements 212. Each transducer element can transmit ultrasound or detect ultrasound echoes. The transducer elements are piezoelectric elements, such as PZT slabs or composites. Alternatively transducer elements are micro-machined in capacitive, polyvinylidene di-fluoride (PVDF) or other materials operable to transduce from electrical to acoustic energy. Only sixteen transducer elements 212 are operative at any point in time.

A controller 200 comprises logic for controlling operation of a pulse generating circuit 220 and the echo detecting circuit 230 and configuring the high voltage multiplexers to operatively connect sixteen transducers 212 of transducer array 210 to the a pulse generating circuit 220 and the echo detecting circuit 230 at any point in time. The controller 200 can be implemented in a field programmable gate array (FPGA) or application specific integrated circuit (ASIC). The controller can also receive information from host computer 112 to allow for configuration and control of the probe 102.

Input/output lines connect the 128 transducer elements to sixteen high voltage multiplexers/demultiplexers of which four are shown HVMUX 250*a*, 250*b*, 250*c*, 250*p*. Each of the sixteen high voltage multiplexers is connected to eight transducer elements. A controller 200 connected to the high voltage multiplexers configures the high voltage multiplexers so that at any point in time each of the sixteen input/output lines (four shown) 252*a*, 252*b*, 252*c*, 252*p* is operatively coupled to exactly one of the 128 transducer elements (sixteen transducers total). Control lines 202 connect the controller 200 to select lines of each of the sixteen HVMUXES 250*a*, 250*b*, 250*c*, 250*p* in order to allow the controller to select which transducer element is operatively connected to the respective HV Pulser at any point in time by input/output lines 252*a*, 252*b*, 252*c*-252*p*. Thus, the probe is physically limited to 16 simultaneous transmit channels at any point in time. The controller 200 selectively configures the high voltage multiplexers to control which sixteen of the 128 transducer elements are operative in any particular send or receive cycle. As further described below the selection of operative elements is changed from cycle to cycle.

The sixteen input/output lines (four shown) 252*a*, 252*b*, 252*c*, 252*p* connect the high voltage multiplexers to both the pulse generating circuit 220 and the echo detecting circuit 230. In a transmit cycle, the pulse generating circuit 220 provides a high voltage pulse to each of the sixteen ultrasound transducers currently connected by the high voltage multiplexers to the sixteen input/output lines causing each of those sixteen ultrasound transducers to emit a pulse of ultrasound. An isolation circuit (not shown) can be used to isolate the echo detecting circuit 230 from the sixteen input/output lines during pulse generation by the pulse generating circuit 220. In a receive cycle the echo detecting circuit 230 detects a signal produced by each of the sixteen ultrasound transducers connected by the high voltage multiplexers to the sixteen input/output lines in response to ultrasound echo energy incident on the transducers.

The pulse generating circuit 220 includes sixteen transmit delay modules (four shown) TX Delay 230*a*, 230*b*, 230*c*, 230*p*. Each transmit delay module is configurable under the control of the controller 200 with a different delay to provide for beam forming and beam steering of the ultrasound beam which will be generated by the sixteen ultrasound transducers operative in a particular transmit cycle. A single transmit command (TXCMD) line is connected to all sixteen of the transmit delay modules. The TXCMD originates from controller 200. The pulse generating circuit also includes sixteen high voltage pulser circuits (four shown) HV Pulser 240*a*, 240*b*, 240*c*, 240*p*. Each transmit delay module is connected to exactly one high voltage pulser circuit.

When a transmit command for a transmit cycle is received on the TXCMD line, each of the transmit delay modules triggers its respective high voltage pulser circuit to output a high voltage pulse on its respective one of the sixteen input/output lines after the configurable delay period. Thus, for each TXCMD a high voltage pulse is applied to each of the sixteen ultrasound transducers currently connected by the high voltage multiplexers to the sixteen input/output lines causing each of those sixteen ultrasound transducers to emit a pulse of ultrasound with the relative timing of the pulses determined by the configurable delays of the sixteen transmit delay modules. The probe thus transmits ultrasound from sixteen transducers during each transmit cycle.

The echo detecting circuit includes sixteen analog to digital converters (four shown) ADC 260a, 260b, 260c, 260p. Each of the sixteen analog to digital converters is connected to a separate one of the sixteen input/output lines. Thus, the probe is physically limited to sixteen simultaneous receive channels at any point in time. In each receive cycle, each of the sixteen analog to digital converters is connected via high voltage muxes to a separate particular one of the transducers as determined by the configuration of the high voltage muxes. Sixteen analog signals generated by the sixteen transducers in response to ultrasound energy incident on the transducers are applied to the sixteen analog to digital converters which generate sixteen digital signals—essentially digital values representing the energy incident on the transducers at a particular point in time.

The sixteen analog to digital converters are connected via sixteen receive delay modules (four shown) 270a, 270b, 270c, 270p to a half line adder 280. The sixteen receive delay modules (four shown) 270a, 270b, 270c, 270p are configurable such that the relative timing of the measurement of the signal for each operative transducer can be controlled. In each receive cycle, sixteen digital values representing the ultrasound energy incident on sixteen operative ultrasound transducers are accumulated in half line adder 280. A selector 281 then allows the sixteen values to be stored in one of two half line buffers 282a and 282b for a total of 32 values. The 32 values are then provided by both half line buffers 282a and 282b to full line adder 284 and full-line buffer 286. The receive channel is thus rendered effectively 32 channel using methods described below despite the fact that only sixteen transducers are operative in any particular transmit and receive cycle.

Essentially, an ultrasonic imaging probe implemented as shown in FIG. 2A utilizes a 32 channel composite aperture which comprises two 16 channel receive apertures used one after the other to receive ultrasound echoes from two identical ultrasound pulses emitted in quick succession and then combined to generate an echo signal equivalent to a 32 channel receive aperture of double the size of the two 16 channel receive apertures individually.

FIG. 2B illustrates operation of the system shown in the block diagram of FIG. 2A. As shown in FIG. 2B, each scan cycle is divided into two transmit cycles and two receive cycles. In the first transmit cycle, the high voltage muxes are configured by signals from controller 200 to connect the sixteen high voltage pulsers to sixteen adjacent transducers 212 of transducer array 210 to produce a first ultrasound pulse. The high voltage muxes are then reconfigured by signal from controller 200 for the first receive cycle such that the echo resulting from the first ultrasound pulse is detected by sixteen ultrasound transducers on the left of the center of the group of transmitting transducers.

In the second transmit cycle the high voltage muxes are reconfigured by signal from controller 200 to connect the sixteen high voltage pulsers to the same sixteen adjacent transducers used in the first transmit cycle to produce a second ultrasound pulse. The high voltage muxes are then reconfigured by signals from controller 200 for the second receive cycle such that the echo resulting from the second ultrasound pulse is detected by sixteen ultrasound transducers on the right of the center of the group of transmitting transducers.

The first and second transmit and receive cycles are conducted in quick succession such that little to no movement of the probe or tissue being measured occurs between the first and second ultrasound pulses for a particular scan line. Two transmit and receive cycles are sequenced in quick succession using a different set of elements for each receive cycle. The signals from both receive cycles are combined into a single signal. Because the times between the two ultrasound pulses is very small compared to the times between scan lines, the non-simultaneity of the two receive cycles is inconsequential. The delay between the first and second transmit ultrasound pulses in the same scan line is selected to be as small as possible while still allowing time for the ultrasound pulse to travel to the depth to be image and an echo to be received.

Referring again to FIG. 2A, the detected signal for the first receive cycle is sent to one of the half line buffers 282a, 282b and the detected signal for the second receive cycle is sent to the other of the half line buffers 282a, 282b. Because little or no movement of the tissue or probe will have occurred between the first and second cycles, the result is 32 channels of received image data for the same tissue is provided to full line adder 284 and full line buffer 286. This allows for full 32 channel output while only using sixteen transducers at any point in time.

To put it another way two ultrasound pulses are emitted in quick succession for each scan line for one set of sixteen ultrasound transducers and then detected by 32 ultrasound transducers where sixteen transducers detect the echo of the first pulse and sixteen different transducers detect the echo of the second pulse. The output of the two sets of sixteen transducers is combined to generate a composite aperture. Each individual RX and TX cycle will use sixteen transducer elements—there are two RX and TX cycles for each scan line resulting in a combined receiving aperture of 32 elements for each scan line. Each scan line is made up of five phases with two transmit cycles and two receive cycles and one adding phase using the full line adder to generate 32 channel output. Between the two receive cycles, twice as many elements as the number of channels is used to create a double-size composite aperture for receiving signals. This is advantageous because it allows the generation of 32 channel output while reducing power consumption by only using 16 channels at any point in time.

After both transmit and receive cycles are completed for a particular scan line, a new vector is selected and the process is repeated for different scan lines having a different selected set of transmitting and receiving transducers. For example, in an embodiment there may be 100 different scan lines (vectors) which are used in combination to generate an image. Where the ultrasound image frame rate is 10 fps, the time between starting consecutive scan lines will be approximately 1000 μs (microseconds). For a depth of 10 cm, and assuming ultrasound speed in the tissue is 1500 m/s or 1.5 mm/μs, the round trip of the ultrasound pulse and echo signal into and back from the tissue is 133 μs. The time between the two transmit cycles in a single scan line is configured to be as small as possible while still allowing detection of the echo signal. The two transmit cycles in each scan line must therefore be spaced by at least 133 μs (for imaging a tissue depth of 10 cm). Thus, there is a significantly shorter time period between the two transmit cycles within a scan line (133 μs) than the time period between consecutive scan lines (1000 μs). In embodiments the time period between transmit cycles in the same scan line is approximately an order of magnitude shorter than the time period between the starts of consecutive scan lines (133 μs compared to 1000 μs).

FIG. 2C illustrates a timeline of transmitting and receiving events for a series of scan line vectors. FIG. 2C illustrates a timeline 290 of events showing the sequence of scan lines and the phases that make up each scan line. FIG. 2C shows first scan line 296a, second scan line 296b, third scan line 296c, and last scan line 296d in a frame 298 (for reference L represents the index of the last scan line in a frame i=E−2N+1). The timeline within each scan line includes a first transmit cycle (e.g. $TX1_1$) with a first set of transducers, a first receive cycle (e.g. $RX1_1$) using a second set of the transducers, a second transmit cycle (e.g. $TX1_2$) using the same first set of the transducers, a second receive cycle (e.g. $RX1_2$) using a third set of the transducers (different than the second set), and then a summing phase (e.g. Adder 1) in which the data from the first and second receive cycles (sixteen channels each) is summed to generate the 32 channel output data.

As discussed above, the time 294 between the first ultrasound pulses of consecutive scan lines is significantly longer than the time between the first and second ultrasound pulse within an individual scan line 292. The time 292 between the first pulse (e.g. $TX1_1$) and the second pulse (e.g. $TX1_2$) within the first scan line is approximately 150 μs. In comparison the time 294 between consecutive scan lines (e.g. the time between $TX1_1$ and $TX1_2$) is approximately 1000 μs (for a framerate or 10 fps assuming 100 scan lines per frame). The time 294 between the start of consecutive scan lines is also substantially larger than the duration 292 of all five phases of a single scan line (approximately 300 μs). After completion of a frame, the system cycles back to the first scan line to commence generation of the next frame of image data.

Signals received in each of the receive cycles of a particular scan line are stored in half line buffers 282a and 282b and combined in full line buffer 286 after both receive cycles have completed. The data from full line buffer 286 can then be transferred to the host computer. The cycles repeat with each incrementing index changing the selection of operative transducers in each scan line until all transducers in the array have been used. To generate scan lines for a particular frame. The process then repeats from the beginning for subsequent frames.

FIGS. 3A-3E illustrate phases of operation of the system shown in the block diagram of FIG. 2A for execution of a single scan line/vector. In FIGS. 3A-3D inactive transducers are shaded whereas active transducers are not.

Figure 3A:
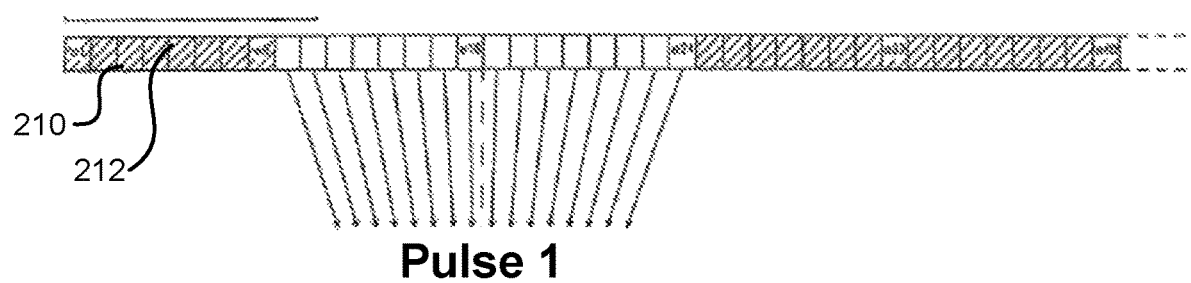
FIGS. 3A-3E illustrate phases of operation of the system shown in the block diagram of FIG. 2A for execution of a single scan line/vector.

FIG. 3A shows phase one of a scan line illustrating the first transmit cycle TX1 for generating the first ultrasound pulse in a 16 channel system. FIG. 3A shows the set of elements selected by the controller to be used in the first transmit cycle of the example 16 channel system. The element set used in the first transmit cycle of the first scan line is made up of transducer elements 9 through 24. As shown in FIG. 3A each of the active elements emit an ultrasound pulse—the ultrasound transducers transmit pulses at times determined by the TX delay modules in order to direct/focus the first ultrasound pulse.

Figure 3B:
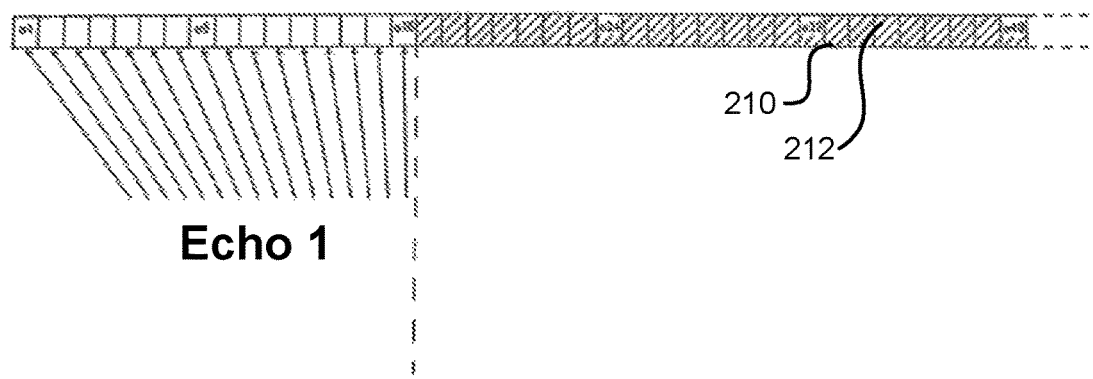

FIG. 3B shows phase two of a scan line illustrating the first receive cycle RX1 for detecting the first ultrasound echo in a 16 channel system. FIG. 3B shows the set of elements selected by the controller to be used in the first receive cycle of the example 16 channel system. The element set used in the first receive cycle of the first scan line is made up of transducer elements 1 through 16. As shown in FIG. 3B each of the active elements detects the first ultrasound echo. The echo is incident on the other elements, but as they are not connected to ADCs, they cannot operatively detect it. The first receive cycle RX1 generates 16 channels of image data.

Figure 3C:
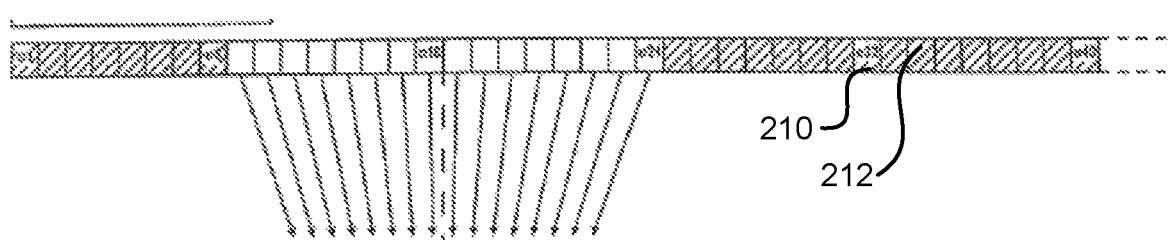

FIG. 3C shows phase three of a scan line illustrating the second transmit cycle TX2 for generating the second ultrasound pulse in a 16 channel system. FIG. 3C shows the set of elements selected by the controller to be used in the second transmit cycle of the example 16 channel system. The element set used in the second transmit cycle of the first scan line is made up of the same transducer elements 9 through 24 active in the first transmit cycle. As shown in FIG. 3C each of the active elements emit an ultrasound pulse—the ultrasound transducers transmit pulses at times determined by the TX delay modules in order to direct/focus the second ultrasound pulse.

Figure 3D:
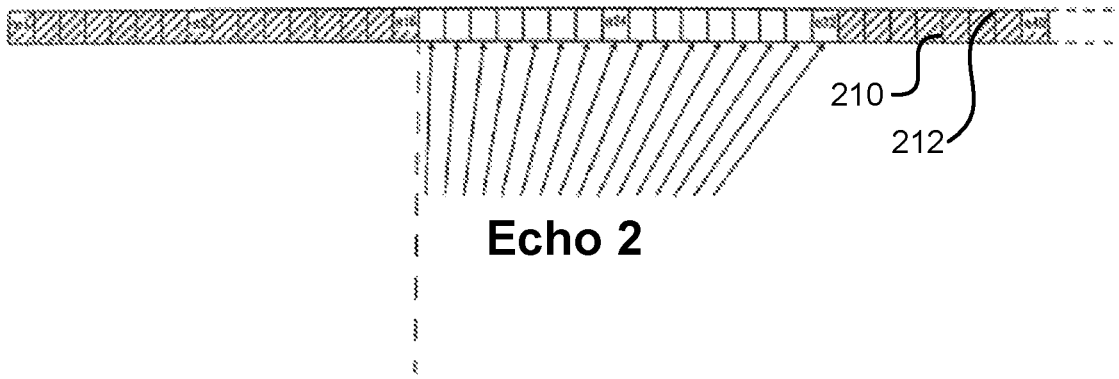

FIG. 3D shows phase four of a scan line illustrating the second receive cycle RX2 for detecting the second ultrasound echo in a 16 channel system. FIG. 3D shows the set of elements selected by the controller to be used in the second receive cycle of the example 16 channel system. The element set used in the second receive cycle of the first scan line is made up of transducer elements 17 through 32. As shown in FIG. 3D each of the active elements detects the second ultrasound echo. The echo is incident on the other elements, but as they are not connected to ADCs, they cannot operatively detect it. The second receive cycle RX2 generates a further 16 channels of image data of the same tissue.

Figure 3E:
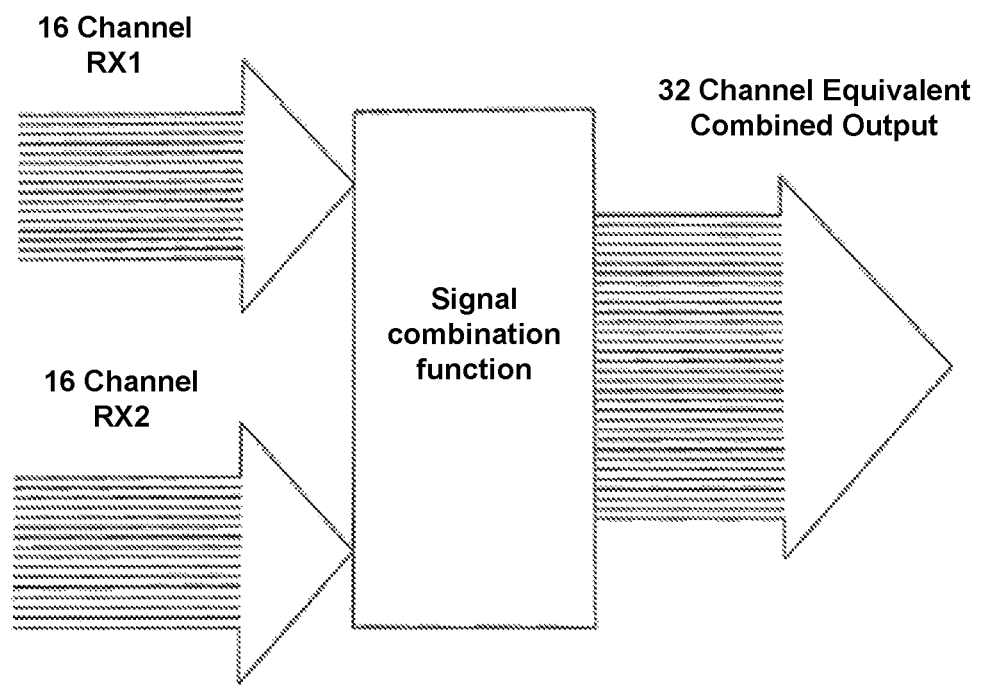

FIG. 3E shows phase five of a scan line illustrating the combination of the 16 channels of image data received in each of the RX1 and RX2 cycles into an equivalent 32 channel image data. As shown in FIG. 3E, the sixteen channels received in RX1 and the 16 channels received in RX2 are combined by signal combination function to provide an equivalent 32 channel combined signal. In a system with 16 physical channels the received signals are processed and combined to create a signal that has equivalent quality to that of a 32 channel system.

After the five phases of the first scan line (i=1) illustrated in FIGS. 3A-3E, the index number is incremented for the next scan line in the frame such that the transducers used in the second scan line are offset by one transducer compared to the first scan line. Thus, the element used in the first and second transmit cycle of the second scan line (i=2) is made up of transducer elements 10 through 25. The element set used in the first receive cycle of the second scan line is made up of transducer elements 2 through 17. The element set used in the second receive cycle of the second scan line is made up of transducer elements 18 through 33.

The index value is incremented from scan line to scan line until that last scan line of a frame (i=E−2N+1) in which the second receive cycle uses the last transducer in the array. The index value is then reset to 1 and the process repeats for the next frame. For example in a 128 transducer array with 16 channels. The element set used in the first and second transmit cycle of the last scan line in a frame (i=97) is made up of transducer elements 105 through 121. The element set used in the first receive cycle of the last scan line is made up of transducer elements 97 through 112. The element set used in the second receive cycle of the last scan line is made up of transducer elements 113 through 128.

The logic for incrementing the index and thus selecting which transducers are active in any particular transmit and receive cycle and scan line is included in controller 200 which uses such logic to determine the signals applied to the select lines of the high voltage muxes 250a, 250b, 250c through 250*p* to connect the selected transducers 212 to the input/output lines 2521, 252*b*, 252*c* through 252*p*. For a 128 element array with 16 channels active at any time the last index number in the frame=128−32+1=97. Thus a single frame will comprise scan lines 1 through 97. Thus a framerate of 10 fps will require approximately 1000 scan lines per second. Accordingly the delay between the start of consecutive scan lines will be approximately 1000 μs.

Although, the examples discussed above utilize an ultrasound transducer with 16 physical channels, composite aperture receiving arrays can be utilized to improve image quality in a wide variety of ultrasound transducer systems having different numbers of transducer elements and different numbers of transmit and receive channels. In a general embodiment, each scan line is made up of five phases with two transmit cycles and two receive cycles. In combination the two receive cycles use twice as many elements as the number of physical channels thereby effectively creating a double size aperture for receiving signals. The set of piezoelectric elements used during each phase is constructed with general equations 1 through 4 provided below. As before the signals received in the second and fourth phases are summed in the fifth phase to generate a results representing the double sized aperture—equation 5.

In the following equations:
E=total number of elements in array
N=number of transmit and receive channels
i=scan beam line index beginning at 1 through (E−2N+1)
e=piezoelectric element number beginning at 1 through E
TX=transmit cycle
RX=receive cycle Equation 1

General form construction of the element set for the first transmit cycle of scan line *i*.

$$TX1_i = \left\{ e \in \mathbb{I} : \left(i + \frac{N}{2}\right) \le e < \left(i + \frac{N}{2} + N\right) \right\} \quad 1$$

Equation 2: General form construction of the element set for the first receive cycle of scan line i.

$$RX1_i = \{ e \varepsilon \, \mathbb{I} : i \le e < (i+N) \} \quad 2$$

Equation 3: General form construction of the element set for the second transmit cycle of scan line i $$TX2_i = TX1_i \quad 3$$

Equation 4: General form construction of the element set for the second receive cycle of scan line i $$RX2_i = \{ e \varepsilon \, \mathbb{I} : (i+N) \le e < (i+2N) \} \quad 4$$

Equation 5: Summation of the first and second received signals into a single 2N channel signal of scan line i $$Signal_i = Signal(RX1_i) + Signal(RX2_i) \quad 5$$

FIG. 4 shows a timing diagram for an example system having sixteen physical channels and 64 transducers in the transducer array. FIG. 4 illustrates a single frame of image data collection having 33 scan lines. Each scan line has five phases including two transmit cycles from the same set of elements (vector), two receive cycles from different sets of elements (vectors) and a summing phase. As described above the delay between the transmit cycles TX1 and TX2 within each scan line is substantially smaller than the delay between TX1 cycles in adjacent scan lines.

Figure 5:
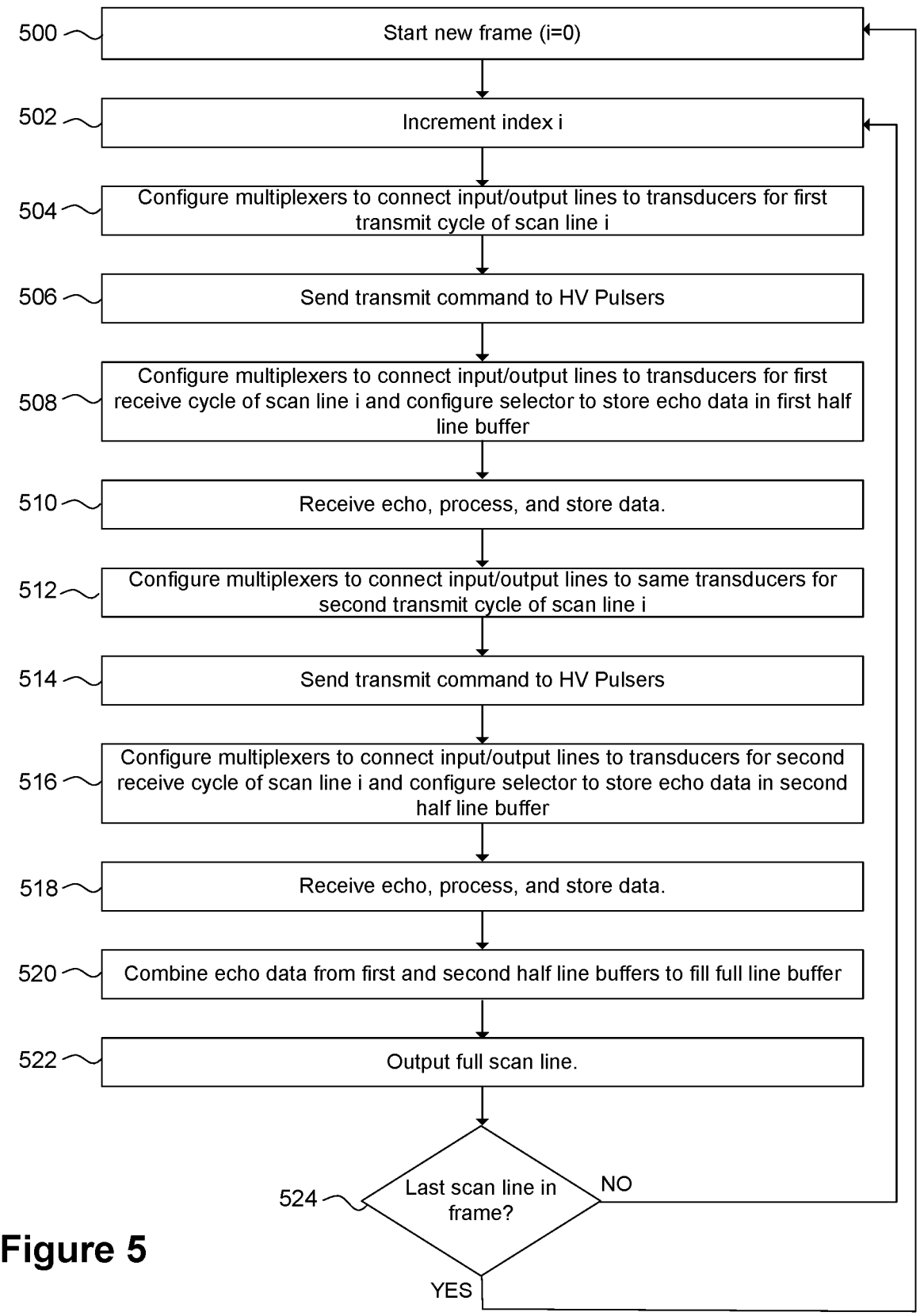
FIG. 5 shows a flowchart illustrating logic for operating an ultrasonic imaging probe according to an embodiment of the present invention.

FIG. 5 shows a flowchart illustrating logic for operating an ultrasonic imaging probe according to an embodiment of the present invention. The logic of FIG. 5 is implemented by controller 200 of FIG. 2A operating the transmit circuits 220 and receive circuits 230 in an embodiment of the invention. The logic of FIG. 5 can be used to select and utilize the element sets constructed according to equations 1-5 provided above. Prior to or during the process shown in FIG. 5, the controller may configure the delays of TX delays 230*a*, 230*b*, 230*c* through 230*p* and RX delays 270*a*, 270*b*, 270*c* through 270*p* as required for focus/beam forming.

As shown in FIG. 5 a frame is commenced at step 500 with the index value set to 0. At step 502 the index value i is incremented. Thus the index value i for the first scan line in the frame is 1. At step 504, the controller configures the HV multiplexers to connect input/output lines to selected transducers 212 for the first transmit cycle of scan line i. The selected transducer set is constructed according to equation 1 above. At step 506, the controller 200 sends a transmit command to the sixteen HV pulsers which produce a high voltage pulse (after the corresponding transmit delay) causing the selected transducer set to emit the first ultrasound pulse of the scan line. At step 508, the controller 200 configures the HV multiplexers to connect input/output lines to selected transducers for the first receive cycle of scan line i, and configures the selector 281 to choose the first half line buffer 282*a*. The selected transducer set is constructed according to equation 2 above. At step 510, the selected transducers 212 receive the echo which is processed by the analog to digital converters in combination with the RX delay circuits and fed through the half line adder 280 and selector 281 to the first half line buffer 282*a*.

At step 512, the controller 200 configures the HV multiplexers to connect input/output lines to selected transducers 212 for the second transmit cycle of scan line i. The transducer set is constructed according to equation 1 above (i.e. the same set of transducers as used in the first transmit cycle of the scan line). At step 514, the controller 200 sends a transmit command to the sixteen HV pulsers which produce a high voltage pulse (after the corresponding transmit delay) causing the selected transducers to emit the second ultrasound pulse of the scan line. At step 516, the controller 200 configures the HV multiplexers to connect input/output lines to selected transducers for the second receive cycle of scan line I, and configures the selector 281 to choose the second half line buffer 282*b*. The selected transducer set is constructed according to equation 4 above. At step 518, the selected transducers 212 receive the echo which is processed by the analog to digital converters in combination with the RX delay circuits and fed through the half line adder to the second half line buffer 282*b*.

At step 520 the full line adder 280 combines the echo data from the first half line buffer 282*a* and second half line 282*b* to fill the full line buffer 286. At step 520 the digital echo data is output from the full line buffer 286. At step 524, if this is not the last scan line in the frame, the process returns to step 502, increments the index i by one and repeats steps 504 to 522 for the next scan line based on the new index value. At step 524, if this is the last scan line in the frame, the process returns to step 500, resets the index value i to zero and begins a new frame. The last scan line has an index value E−2N+1 as described above for the general case.

The foregoing description of preferred embodiments of the present invention has been provided for the purposes of illustration and description. It is not intended to be exhaustive or to limit the invention to the precise forms disclosed. Many modifications and variations will be apparent to one of ordinary skill in the relevant arts. The above mentioned part numbers are exemplary, and are not meant to be limiting. Accordingly, other parts can be substituted for those mentioned above.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

The invention claimed is:

1. A method for operating a portable ultrasound probe, the method comprising:
   providing a portable ultrasound probe having a plurality of ultrasound transducers therein, the plurality of ultrasound transducers arranged in an linear array, the portable ultrasound probe further comprising sixteen transmit channels, sixteen receive channels, a first half line buffer, a second half line buffer and a full line buffer;
   wherein each of the sixteen transmit channel comprises a high voltage pulser and wherein each of the sixteen receive channels comprises an analog to digital (ADC) converter;
   connecting a first sixteen of the plurality of ultrasound transducers to the sixteen transmit channels;
   emitting a first high voltage pulse from the high voltage pulsers to cause the first sixteen ultrasound transducers to emit a first ultrasound pulse;
   connecting a second sixteen of the plurality of ultrasound transducers to the sixteen receive channels, each of the sixteen receive channels comprising one of said sixteen ADC;
   detecting a first ultrasound echo with said second sixteen ultrasound transducers, converting said echo with said sixteen ADC, and storing sixteen channels of digital echo data in the first half line buffer;
   connecting the first sixteen ultrasound transducers to the sixteen transmit channels;
   emitting a second high voltage pulse from sixteen high voltage pulsers to cause the first sixteen ultrasound transducers to emit a second ultrasound pulse;
   connecting a third sixteen of the plurality of ultrasound transducers to the same sixteen receive channels, each of the same sixteen receive channels comprising the same one of said sixteen ADC;
   detecting a second ultrasound echo with third sixteen ultrasound transducers, converting said echo with said sixteen ADC, and storing a second sixteen channels of digital echo data in the second half line buffer;
   combining the first sixteen channels of digital echo data in the first half line buffer and the second sixteen channels of digital echo data in the second half line buffer and storing thirty-two channels of digital echo data in the full line buffer;
   outputting thirty-two channels of digital echo data from the full-line buffer to a system for generating an ultrasound image.

2. The method of claim 1, wherein the second ultrasound pulse is emitted less than 200 µs after the first ultrasound pulse.

3. The method of claim 1, further comprising:
   connecting a fourth sixteen of the plurality of ultrasound transducers to the sixteen transmit channels, wherein the fourth sixteen transducers are translated one ultrasound transducer along the array relative to the first sixteen ultrasound transducers;
   emitting a first high voltage pulse from the high voltage pulsers to cause the fourth sixteen ultrasound transducers to emit a third ultrasound pulse;
   connecting a fifth sixteen of the plurality of ultrasound transducers to the sixteen receive channels, wherein the fifth sixteen transducers are translated one ultrasound transducer along the array relative to the second sixteen ultrasound transducers;
   detecting a third ultrasound echo with said fifth sixteen ultrasound transducers, converting said echo with said sixteen ADC, and storing a third sixteen channels of digital echo data in the first half line buffer;
   connecting the fourth sixteen ultrasound transducers to the sixteen transmit channels;
   emitting a fourth high voltage pulse from the sixteen high voltage pulsers to cause the fourth sixteen ultrasound transducers to emit a fourth ultrasound pulse;
   connecting a sixth sixteen of the plurality of ultrasound transducers to the sixteen receive channels, wherein the sixth sixteen transducers are translated one ultrasound transducer along the array relative to the third sixteen ultrasound transducers;
   detecting a fourth ultrasound echo with sixth sixteen ultrasound transducers, converting said echo with said sixteen ADC, and storing a fourth sixteen channels of digital echo data in the second half line buffer;
   combining the third sixteen channels of digital echo data in the first half line buffer and the fourth sixteen channels of digital echo data in the second half line buffer and storing a second thirty-two channels of digital echo data in the full line buffer;
   outputting the second thirty-two channels of digital echo data from the full-line buffer to a system for generating an ultrasound image.

4. The method of claim 1, further comprising performing the following steps more than 200 µs after emitting the second high voltage pulse:
   connecting a fourth sixteen of the plurality of ultrasound transducers to the sixteen transmit channels, wherein the fourth sixteen transducers are translated one ultrasound transducer along the array relative to the first sixteen ultrasound transducers;
   emitting a first high voltage pulse from the high voltage pulsers to cause the fourth sixteen ultrasound transducers to emit a third ultrasound pulse;
   connecting a fifth sixteen of the plurality of ultrasound transducers to the sixteen receive channels, wherein the fifth sixteen transducers are translated one ultrasound transducer along the array relative to the second sixteen ultrasound transducers;
   detecting a third ultrasound echo with said fifth sixteen ultrasound transducers, converting said echo with said sixteen ADC, and storing a third sixteen channels of digital echo data in the first half line buffer;
   connecting the fourth sixteen ultrasound transducers to the sixteen transmit channels;
   emitting a fourth high voltage pulse from the sixteen high voltage pulsers to cause the fourth sixteen ultrasound transducers to emit a fourth ultrasound pulse;
   connecting a sixth sixteen of the plurality of ultrasound transducers to the sixteen receive channels, wherein the sixth sixteen transducers are translated one ultrasound transducer along the array relative to the third sixteen ultrasound transducers;

detecting a fourth ultrasound echo with sixth sixteen ultrasound transducers, converting said echo with said sixteen ADC, and storing a fourth sixteen channels of digital echo data in the second half line buffer;

combining the third sixteen channels of digital echo data in the first half line buffer and the fourth sixteen channels of digital echo data in the second half line buffer and storing a second thirty-two channels of digital echo data in the full line buffer;

outputting the second thirty-two channels of digital echo data from the full-line buffer to a system for generating an ultrasound image.

5. The method of claim 1, wherein:
the linear array comprises a linear array of micro-machined ultrasound transducers formed on a common substrate.

6. The method of claim 1, wherein:
the linear array comprises a linear array of separately formed ultrasound transducers mounted on a common support.

7. The method of claim 1, wherein the second sixteen ultrasound transducers are immediately adjacent the third sixteen ultrasound transducers on the linear array.

8. The method of claim 1, wherein the second sixteen ultrasound transducers are immediately adjacent the third sixteen ultrasound transducers on the linear array and the first sixteen ultrasound transducers comprises half of the second sixteen ultrasound transducers and half of the third sixteen ultrasound transducers.

9. The portable ultrasound probe of claim 8, configured to emit the second ultrasound pulse less than 200 μs after emitting the first ultrasound pulse.

10. The portable ultrasound probe of claim 8, wherein the portable ultrasound probe is further configured to:
connect a fourth sixteen of the plurality of ultrasound transducers to the sixteen transmit channels, wherein the fourth sixteen transducers are translated one ultrasound transducer along the array relative to the first sixteen ultrasound transducers;
emit a third high voltage pulse from the high voltage pulsers to cause the fourth sixteen ultrasound transducers to emit a third ultrasound pulse;
connect a fifth sixteen of the plurality of ultrasound transducers to the sixteen receive channels, wherein the fifth sixteen transducers are translated one ultrasound transducer along the array relative to the second sixteen ultrasound transducers;
detect a third ultrasound echo with said fifth sixteen ultrasound transducers, convert said echo with said sixteen ADC, and store a third sixteen channels of digital echo data in the first half line buffer;
connect the fourth sixteen ultrasound transducers to the sixteen transmit channels;
emitting a fourth high voltage pulse from the sixteen high voltage pulsers to cause the fourth sixteen ultrasound transducers to emit a fourth ultrasound pulse;
connect a sixth sixteen of the plurality of ultrasound transducers to the sixteen receive channels, wherein the sixth sixteen transducers are translated one ultrasound transducer along the array relative to the third sixteen ultrasound transducers;
detecting a fourth ultrasound echo with sixth sixteen ultrasound transducers, convert said echo with said sixteen ADC, and store a fourth sixteen channels of digital echo data in the second half line buffer;
combining the third sixteen channels of digital echo data in the first half line buffer and the fourth sixteen channels of digital echo data in the second half line buffer and store a second thirty-two channels of digital echo data in the full line buffer;
output the second thirty-two channels of digital echo data from the full-line buffer to a system for generating an ultrasound image.

11. The portable ultrasound probe of claim 8, wherein the portable ultrasound probe is further configured to perform the following more than 200 μs after emitting the second high voltage pulse:
connect a fourth sixteen of the plurality of ultrasound transducers to the sixteen transmit channels, wherein the fourth sixteen transducers are translated one ultrasound transducer along the array relative to the first sixteen ultrasound transducers;
emit a third high voltage pulse from the high voltage pulsers to cause the fourth sixteen ultrasound transducers to emit a third ultrasound pulse;
connect a fifth sixteen of the plurality of ultrasound transducers to the sixteen receive channels, wherein the fifth sixteen transducers are translated one ultrasound transducer along the array relative to the second sixteen ultrasound transducers;
detect a third ultrasound echo with said fifth sixteen ultrasound transducers, convert said echo with said sixteen ADC, and store a third sixteen channels of digital echo data in the first half line buffer;
connect the fourth sixteen ultrasound transducers to the sixteen transmit channels;
emitting a fourth high voltage pulse from the sixteen high voltage pulsers to cause the fourth sixteen ultrasound transducers to emit a fourth ultrasound pulse;
connect a sixth sixteen of the plurality of ultrasound transducers to the sixteen receive channels, wherein the sixth sixteen transducers are translated one ultrasound transducer along the array relative to the third sixteen ultrasound transducers;
detecting a fourth ultrasound echo with sixth sixteen ultrasound transducers, convert said echo with said sixteen ADC, and store a fourth sixteen channels of digital echo data in the second half line buffer;
combining the third sixteen channels of digital echo data in the first half line buffer and the fourth sixteen channels of digital echo data in the second half line buffer and store a second thirty-two channels of digital echo data in the full line buffer;
output the second thirty-two channels of digital echo data from the full-line buffer to a system for generating an ultrasound image.

12. The portable ultrasound probe of claim 8, wherein:
the linear array of ultrasound transducers comprises a linear array of micro-machined ultrasound transducers formed on a common substrate.

13. The portable ultrasound probe of claim 8, wherein:
the linear array of ultrasound transducers comprises a linear array of separately formed ultrasound transducers mounted on a common support.

14. A portable ultrasound probe comprising:
a linear array of ultrasound transducers within the portable ultrasound probe;
sixteen transmit channels wherein each of the sixteen transmit channel comprises a high voltage pulser;
sixteen receive channels wherein each of the sixteen receive channels comprises an analog to digital (ADC) converter;
a first half line buffer
a second half line buffer; and a full line buffer;
wherein the portable ultrasound probe is configured to perform steps comprising,
connecting a first sixteen of the ultrasound transducers to the sixteen transmit channels;
emitting a first high voltage pulse from the high voltage pulsers to cause the first sixteen ultrasound transducers to emit a first ultrasound pulse;
connecting a second sixteen of the ultrasound transducers to the sixteen receive channels, each of the sixteen receive channels comprising one of the said;
detecting a first ultrasound echo with said second sixteen ultrasound transducers, converting said echo with said sixteen ADC, and storing sixteen channels of digital echo data in the first half line buffer;
connecting the first sixteen ultrasound transducers to the sixteen transmit channels;
emitting a second high voltage pulse from sixteen high voltage pulsers to cause the first sixteen ultrasound transducers to emit a second ultrasound pulse;
connecting a third sixteen of the ultrasound transducers to the same sixteen receive channels, each of the same sixteen receive channels comprising one of the same said sixteen ADC;
detecting a second ultrasound echo with third sixteen ultrasound transducers, converting said echo with said sixteen ADC, and storing a second sixteen channels of digital echo data in the second half line buffer;
combining the first sixteen channels of digital echo data in the first half line buffer and the second sixteen channels of digital echo data in the second half line buffer and storing thirty-two channels of digital echo data in the full line buffer;
outputting thirty-two channels of digital echo data from the full-line buffer to a system for generating an ultrasound image.

15. A portable ultrasound probe comprising:
a linear array of ultrasound transducers contained in portable ultrasound probe;
sixteen transmit channels wherein each of the sixteen transmit channel comprises a high voltage pulser;
sixteen receive channels wherein each of the sixteen receive channels comprises an analog to digital (ADC) converter;
a first half line buffer
a second half line buffer; and
a full line buffer;
wherein the portable ultrasound probe is configured to use the sixteen transmit channels to cause a first sixteen ultrasound transducers in the linear array to emit a first and second ultrasound pulse within 200 µs;
wherein the portable ultrasound probe is configured to detect a first ultrasound echo corresponding to the first ultrasound pulse with a second sixteen ultrasound transducers connected to the sixteen receive channels and convert said echo with said sixteen ADC, and store a first sixteen channels of digital echo data in the first half line buffer;
wherein the portable ultrasound probe is configured to detect a second ultrasound echo corresponding to the second ultrasound pulse with a third sixteen ultrasound transducers connected to the same sixteen receive channels and convert said echo with said same sixteen ADC, and store a second sixteen channels of digital echo data in the second half line buffer;
wherein the portable ultrasound probe is configured to combine the first sixteen channels of digital echo data in the first half line buffer and the second sixteen channels of digital echo data in the second half line buffer and store thirty-two channels of digital echo data in the full line buffer, and then output the thirty-two channels of digital echo data from the full-line buffer to a system for generating an ultrasound image.

16. The portable ultrasound probe of claim 15, wherein:
the linear array of ultrasound transducers comprises a linear array of micro-machined ultrasound transducers formed on a common substrate.

17. The portable ultrasound probe of claim 15, wherein:
the linear array of ultrasound transducers comprises a linear array of separately formed ultrasound transducers mounted on a common support.

* * * * *